United States Patent
Robichaud

(10) Patent No.: US 10,285,784 B2
(45) Date of Patent: May 14, 2019

(54) METHOD OF DESIGNING A MANDIBULAR ADVANCEMENT DEVICE AND MANDIBULAR ADVANCEMENT DEVICE

(71) Applicant: Panthera Dental Inc., Québec (CA)

(72) Inventor: Jean Robichaud, Quebec (CA)

(73) Assignee: Panthera Dental Inc., Quebec (CA)

( * ) Notice: Subject to any disclaimer, the term of this patent is extended or adjusted under 35 U.S.C. 154(b) by 41 days.

(21) Appl. No.: 15/204,640

(22) Filed: Jul. 7, 2016

(65) Prior Publication Data

US 2017/0007371 A1    Jan. 12, 2017

(30) Foreign Application Priority Data

Jul. 7, 2015   (FR) ...................... 15 56415

(51) Int. Cl.
*A61C 7/08* (2006.01)
*A61C 7/36* (2006.01)
(Continued)

(52) U.S. Cl.
CPC ............... *A61C 7/36* (2013.01); *A61C 7/002* (2013.01); *A61C 7/08* (2013.01); *A61F 5/566* (2013.01); *G06F 19/00* (2013.01); *G16H 50/50* (2018.01)

(58) Field of Classification Search
CPC .............................. A61C 7/08; A61C 13/0004
See application file for complete search history.

(56) References Cited

U.S. PATENT DOCUMENTS 4,551,095 A   11/1985 Mason
5,011,404 A   4/1991 Losi
(Continued)

FOREIGN PATENT DOCUMENTS

CA    2791139 A1 *  3/2014   ............... A61C 7/36
CH    682883 A5    12/1993
(Continued)

OTHER PUBLICATIONS

Taugerbeck, "Comparison of Dental Intraloral Devices for Snoring Therapy : A Subjective Survey of their Effect on Mixed Sleep Apnea Syndrome", Patients and Doctors Forum, 1997, pp. 20-31.
(Continued)

*Primary Examiner* — Thomas L Dickey
(74) *Attorney, Agent, or Firm* — Marshall, Gerstein & Borun LLP

(57) ABSTRACT

Method for determining a patient's open-position occlusal plane comprising: obtaining a global model of the patient's jaw including a model of the mandible and maxilla in articulation; determining a natural occlusal plane of the patient from a global model of the patient's jaw in a centric occlusion position; determining a necessary opening to enable the advancement of the patient's mandible; determining a mandibular virtual plane from the global model of the patient's jaw in an open position based on the necessary opening determined; and determining the open-position occlusal plane from the mandibular virtual plane, the natural occlusal plane and the global model of the jaw in the open position based on the necessary opening determined. A method of designing a mandibular advancement device for a patient based on the open-position occlusal plane is also described as well as the resulting mandibular advancement device.

20 Claims, 11 Drawing Sheets

(51) Int. Cl.
*A61F 5/56* (2006.01)
*A61C 7/00* (2006.01)
*G16H 50/50* (2018.01)
*G06F 19/00* (2018.01)

(56) References Cited

U.S. PATENT DOCUMENTS

| | | | |
|---|---|---|---|
| 5,879,157 | A | 3/1999 | Scheu |
| 5,947,724 | A | 9/1999 | Frantz et al. |
| 6,012,920 | A | 1/2000 | Woo |
| 6,055,986 | A | 5/2000 | Meade |
| 6,109,265 | A | 8/2000 | Frantz et al. |
| 6,234,792 | B1 | 5/2001 | DeVincenzo |
| 6,302,686 | B1 | 10/2001 | Chott et al. |
| 6,418,933 | B1 | 7/2002 | Strong |
| 7,987,854 | B2 | 8/2011 | Arni |
| 8,646,454 | B1 | 2/2014 | Moses et al. |
| 2001/0036615 | A1 | 11/2001 | Binder |
| 2005/0016547 | A1* | 1/2005 | Mousselon ............ A61F 5/566 128/861 |
| 2006/0121407 | A1 | 6/2006 | Dylina |
| 2007/0183572 | A1 | 8/2007 | Drummond et al. |
| 2013/0066598 | A1 | 3/2013 | Fisker et al. |
| 2013/0140289 | A1 | 6/2013 | Baratier et al. |
| 2013/0275107 | A1 | 10/2013 | Alpern et al. |
| 2014/0326253 | A1* | 11/2014 | Baratier ................ A61F 5/566 128/848 |

FOREIGN PATENT DOCUMENTS

| | | |
|---|---|---|
| CN | 2418850 Y | 2/2001 |
| DE | 29506512 U1 | 6/1995 |
| DE | 19746157 C2 | 3/1999 |
| DE | 20102432 U1 | 4/2001 |
| EP | 0794749 B1 | 6/2003 |
| EP | 1459699 A1 | 9/2004 |
| EP | 1516604 A1 | 3/2005 |
| EP | 2143397 A1 | 1/2010 |
| WO | 0238090 A1 | 5/2002 |
| WO | 03034957 A2 | 5/2003 |

OTHER PUBLICATIONS

Dischinger. "Edgewise Herbst Appliance", JCO, Inc., vol. 29, No. 12, 1995, pp. 738-742.
Sanner et al., "Oral Appliances for the treatment of Obstructive Sleep Apnea", Somnologie, vol. 3, 1999, pp. 62-66.
Bloch et al. "A Randomized, Controlled Crossover Trial of Two Oral Appliances for Sleep Apnea Treatment", American Journal of Respiratory and Critical Care Medicine, vol. 162., 2000, pp. 246-251.
Rose, "Die Wertigkeit oraler Therapie-verfahren zur Behandlung des Schnarchens and der obstruktiven Schlafapnoe", Scheweiz Monatsschr Zahnmed. vol. 112. No. 4, 2001, pp. 359-365.
Rogers, "Troubleshooting the Herbst Appliance", JCO, Inc., vol. XXXVI, No. 5, May 2002, pp. 268-274.
Randerath et al., "An Individually Adjustable Oral Appliance vs Continuous Positive Airway Pressure in Mild-to-Moderate Obstructive Sleep Apnea Syndrome", Chest Journal, vol. 122, vol. 2, 2002, pp. 569-575.
Petelle et al., "One-Night Mandibular Advancement Titration for Obstructive Sleep Apnea Syndrome—A Pilot Study", American Journal of Respiratory and critical care medicine, vol. 165, 2002, pp. 1150-1153.
Langenhan et al."Beiträge aus der Quintessenz und der Quintessenz Zahntechnik", Quintessenz, Focus Zahnmedizin, Schlafapnoe, 2010, pp. 1-16.
Langenhan et al, "Intraorale Protrusionsschienen bei OSAS und Schnarchen—Aktualisierte zahnmedizinische und zahntechnische Standards", Quintessenz Zahntech, vol. 36, No. 6, 2010, pp. 774-790.

\* cited by examiner

METHOD OF DESIGNING A MANDIBULAR ADVANCEMENT DEVICE AND MANDIBULAR ADVANCEMENT DEVICE

CROSS-REFERENCE TO RELATED APPLICATIONS

This application claims priority of French patent application 1556415 filed on Jul. 7, 2015, the specification of which is hereby incorporated by reference.

FIELD OF THE INVENTION

This invention relates to a method of designing a mandibular advancement device. It also relates to mandibular advancement device designed according to this method.

BACKGROUND

During sleep, a muscular relaxation in the throat area occurs in humans thus causing a narrowing of the pharynx. In some individuals, this narrowing creates an airflow problem and can cause a noise called "snoring," which can reach 90 decibels.

In certain cases, this narrowing can be so great that respiration is suspended for a certain period of time. This phenomenon of respiratory arrest is called "sleep apnea."

There are numerous devices that prevent snoring and sleep apnea. Among the existing devices, one of the most effective is a dental device that enables the advancement of the mandible, often referred to as a mandibular protrusion device (or splint) or mandibular advancement device (or splint). This advancement of the mandible allows the opening of the pharynx to be maintained as much as possible, i.e. to minimize the narrowing thereof during muscular relaxation.

There are different types of dental appliances enabling advancement of the mandible. Some comprise two gutters, independent of one another and adapted to the top and bottom teeth respectively. These two gutters are connected by two retaining rods (often referred to as "retaining bars" or "connecting bars"). The retaining rods are fixed to the upper gutter at the canines and to the lower gutter at the first or second molars. The length of the retaining rods is chosen so that, when the device is in the mouth, the patient's jaw is kept in an advanced position.

As shown in FIG. 1, the temporomandibular articulation (TMA, or temporomandibular condyle) is a movable (or synovial) articulation that joins the mandibular fosse of the temporal bone to the condyle of the mandible by means of a fibrocartilaginous articular disc. On opening the mouth, a rotational movement of the mandibular condyle in the TMA capsule occurs. This movement is, in principle, natural and causes no pain.

As shown in FIG. 2, when the mandible in kept an advanced position, the TMA also adopts an advanced position. This advancement of the TMA can sometimes cause the patient pain.

Moreover, numerous cases of the gutters unhooking during sleep are observed. This unhooking is due to the fact that the retaining rods are positioned obliquely, in a bad position and sometimes too rigid. When the gutters unhook, the device is expelled from its protrusion position and the patient is no longer treated.

Some intraoral devices include a system for adjusting the retaining rods. However, they are usually difficult to check, i.e. it is difficult to know precisely the distance (in millimeters) of advancement of the lower jaw. Now, the advancement of the mandible (lower jaw) is the key to success for a mandibular advancement device to prevent snoring and obstructive sleep apnea. Moreover, the TMA is sensitive to each half-millimeter of advancement and each half-millimeter of advancement is very important for a patient sensitive to pain.

In order to enable the mandible to adopt an advanced position, the mandible must be open so that it can pass over all of the cusps of the upper and lower teeth. Thus, mandibular advancement devices have the effect of holding the jaw, for several hours, in an open position and of keeping the bone condyle in an advanced and unnatural position in the capsule, as shown in FIG. 2. In order to pass over all of the cusps of the upper and lower teeth, the opening of the jaw created by the devices is often from 3 to 4 millimeters and sometimes more, which is considerable. Consequently, it is important that the retaining rods connecting the gutters of the device work as far as possible in the same plane as that of the TMA.

With reference to FIG. 3, the natural occlusal plane (or occlusal plane) 20 of a patient is defined as a virtual surface that corresponds to the centric occlusion of a patient. More particularly, it is defined by the area of confrontation of the antagonist teeth, i.e. when the occlusal surfaces of the teeth of the mandible and maxilla are in contact, tangent to the incisal edges and the cusp points of the premolars and molars of each jaw. The natural occlusal plane 20 therefore respects the position of the patient's natural TMA, shown in FIG. 1.

The majority of devices are designed without considering a patient's natural occlusal plane 20. Some devices, however, are designed so that they approximately respect this plane, although there is currently no way of allowing a device to precisely respect the patient's occlusal plane. Moreover, with an approximate opening of 3 to 4 millimeters, the patient's natural occlusal plane 20 is no longer valid.

SUMMARY OF THE INVENTION

Consequently, one aim of the present invention is to provide methods and mandibular advancement devices to overcome at least one drawback of the prior art.

According to one general aspect, there is provided a method for determining a patient's open-position occlusal plane. This method comprises: obtaining a global model of the patient's jaw including a model of the mandible and maxilla in articulation; determining a natural occlusal plane of the patient from the global model of the patient's jaw in a centric occlusion position; determining a necessary opening to enable the advancement of the patient's mandible; determining a mandibular virtual plane from the global model of the patient's jaw in an open position based on the necessary opening determined; and determining the open-position occlusal plane from the mandibular virtual plane, the natural occlusal plane and the global model of the jaw in the open position based on the necessary opening determined.

In one embodiment, determination of the open-position occlusal plane comprises determining a center line between the mandibular virtual plane and the natural occlusal plane in the open position based on the necessary opening determined, the center line extending between a posterior section and an anterior section of the global model of the patient's jaw.

In one embodiment, determination of the open-position occlusal plane comprises representing the open-position occlusal plane in the global model of the patient's jaw in the open position based on the necessary opening determined.

In one embodiment, determination of the necessary opening comprises representing the global model of the patient's jaw in the open position based on the necessary opening determined.

In one embodiment, determination of the open-position occlusal plane comprises representing the natural occlusal plane in the global model of the patient's jaw in the open position based on the necessary opening determined.

In one embodiment, determination of the mandibular virtual plane in the open position comprises representing the mandibular virtual plane in the global model of the patient's jaw in the open position.

In one embodiment, determination of the patient's natural occlusal plane from the global model of the patient's jaw comprises: configuring the global model of the patient's jaw in the centric occlusion position and defining a line extending between occlusal faces of the teeth of the mandible and maxilla in contact, tangential to incisal edges, at cusp points of pre-molars and molars of upper jaw and lower jaw. This method further comprises defining a point of maxillary contact corresponding to the intersection of the natural occlusal plane on incisors of the maxilla in the centric occlusion position and a mandibular contact point corresponding to an intersection of the natural occlusal plane on incisors of the mandible in the centric occlusion position. Determination of the mandibular virtual plane in the open position comprises defining a line extending between the occlusal face of at least one of molars and premolars of the mandible and the mandibular contact point on the mandibular incisors.

In one embodiment, determination of the necessary opening comprises estimating a distance enabling incisors of the mandible to be advanced without interfering with incisors of the maxilla.

In one embodiment, obtaining the global model of the jaw comprises: obtaining a model of the mandible and a model of the maxilla; obtaining a model of centric occlusion; and combining the model of the mandible, the model of the maxilla and the model of the centric occlusion in order create the global model of the patient's jaw in which the models of the mandible and maxilla are in articulation. Obtaining the model of the mandible and the model of the maxilla comprises performing an optical scan of the mandible and maxilla or of a physical model of the mandible and maxilla. Obtaining the centric occlusion model comprises performing an optical scan of the mandible and maxilla in the centric occlusion position or of the physical model of the mandible and maxilla in the centric occlusion position.

According to another general aspect, there is provided a method of designing a mandibular advancement device for a patient including a lower gutter and an upper gutter. This method comprises: determining the patient's open-position occlusal plane using the method described above; determining retaining pins for the mandibular advancement device, the retaining pins having a centric line, an anterior anchorage, a posterior anchorage and a length L between the anterior anchorage and the posterior anchorage; positioning the anterior and posterior anchorages so that the centric line of the retaining pins extends in a substantially parallel manner above the patient's open-position occlusal plane; and designing the lower gutter and the upper gutter of the device using the global model of the patient's jaw and in a manner such that the anterior anchorages of the retaining pins are connectable to the upper gutter and in a manner such that the posterior anchorages of the retaining pins are connectable to the lower gutter.

In one embodiment, the method comprises obtaining a patient's maximum advancement and positioning the model of the mandible and maxilla in the open position in an advanced position of the mandible by a movement along the open-position occlusal plane for a distance corresponding to the patient's maximum advancement. Determining the retaining pins and positioning the anterior and posterior anchorages is achieved on the model of the mandible and maxilla in the open advanced position using the patient's maximum advancement.

In one embodiment, positioning the anterior and posterior anchorages comprises: positioning the anterior anchorage of each of the retaining pins in relation to a respective canine of maxillary canines on the global model of the jaw; and positioning the posterior anchorage of each of the retaining pins in a manner such that the centric line of the retaining pins extends substantially parallel to the open-position occlusal plane on the global model of the patient's jaw. Positioning the posterior anchorage comprises determining a posterior position to the anterior anchorage, by a distance corresponding to the length L, in a direction parallel to the open-position occlusal plane on the global model of the patient's jaw in the open position.

In one embodiment, designing the lower gutter comprises designing an extension extending over the occlusion surfaces in the posterior sections aligned with the posterior anchorage of one of the retaining pins.

In one embodiment, determining the necessary opening comprises estimating the distance that allows incisors of the mandible to be advanced without interfering with incisors of the maxilla including the thickness of the upper gutter and the lower gutter of the device.

According to still another general aspect, there is provided a mandibular advancement device. The mandibular advancement device comprises: an upper gutter and a lower gutter designed to cover at least partially and respectively teeth and/or upper and lower jaws, and two retaining pins connecting the lower gutter and the upper gutter, the retaining pins extending parallel to and over the open-position occlusal plane, determined by the method described above, the retaining pins being of a length enabling the lower jaw to be kept in an advanced position in relation to the upper jaw when wearing the device.

In one embodiment, the lower gutter and the upper gutter comprise flat surfaces at occlusion faces of posterior teeth. The flat surfaces of the upper gutter are shorter than the flat surfaces of the lower gutter.

In one embodiment, the flat surfaces of the upper gutter extend approximately from a maxillary canine and posteriorly until at least a distal of a first premolar.

In one embodiment, the flat surfaces of the upper gutter extend posteriorly at most to a distal of a second premolar.

According to still another general aspect, there is provided a mandibular advancement device. The mandibular advancement device comprises: an upper gutter and a lower gutter designed to cover at least partially and respectively teeth and/or upper and lower jaw, and two retaining pins connecting the lower gutter and the upper gutter, the upper gutter, the lower gutter and the retaining pins being conceived according to the method described above.

In one embodiment, the lower gutter and the upper gutter comprise flat surfaces at occlusion faces of posterior teeth. The flat surfaces of the upper gutter are shorter than the flat surfaces of the lower gutter.

In one embodiment, the flat surfaces of the upper gutter extend approximately from a maxillary canine and posteriorly until at least a distal of a first premolar.

In one embodiment, the flat surfaces of the upper gutter extend posteriorly at most to a distal of a second premolar.

According to still another general aspect, there is provided an intraoral device. The intraoral device comprises an upper gutter and a lower gutter designed to cover at least partially and respectively teeth and/or upper and lower jaws, and two retaining pins connecting the lower gutter and the upper gutter and of a length enabling the lower jaw to be kept in an open and advanced position in relation to the upper jaw and positioned parallel to an open-position occlusal plane determined by an opening necessary to advance and keep the lower jaw in the open and advanced position.

In one embodiment, the lower gutter and the upper gutter comprise flat surfaces at occlusion faces of the posterior teeth. The flat surfaces of the upper gutter are shorter than the flat surfaces of the lower gutter.

In one embodiment, the flat surfaces of the upper gutter extend approximately from a maxillary canine and posteriorly until at least a distal of a first premolar.

In one embodiment, the flat surfaces of the upper gutter extend posteriorly at most to a distal of a second premolar.

DETAILED DESCRIPTION

A mandibular (protrusion) advancement device 40 and a method of designing a mandibular advancement device will be described with reference to the Figures.

Figure 1:
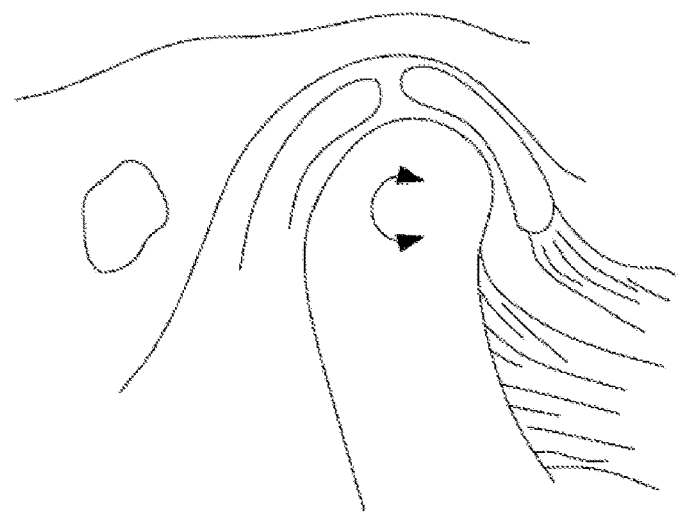
FIG. 1 is a schematic view of a temporomandibular condyle (TMA) in a normal position.
Figure 2:
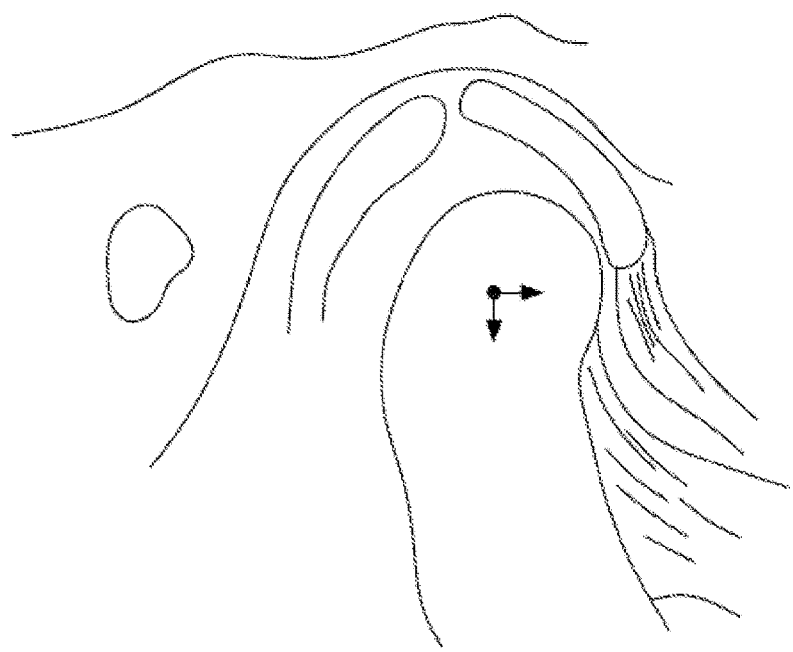
FIG. 2 is a schematic view of a temporomandibular condyle (TMA) in an advanced position.
Figure 3A:
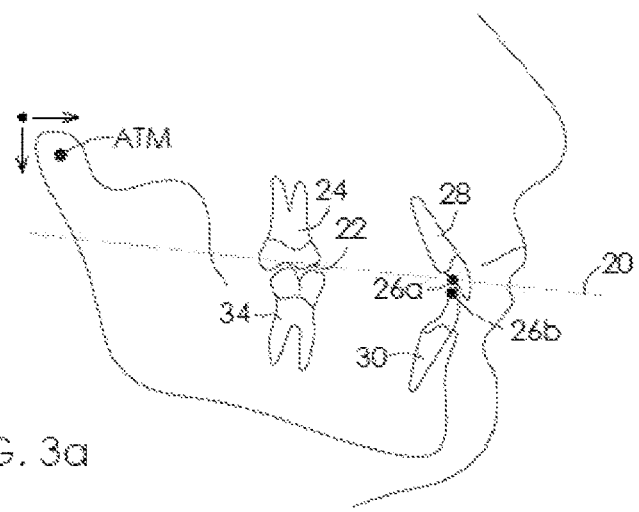
FIG. 3a is a schematic view of a patient's natural occlusal plane including the TMA.
Figure 3B:
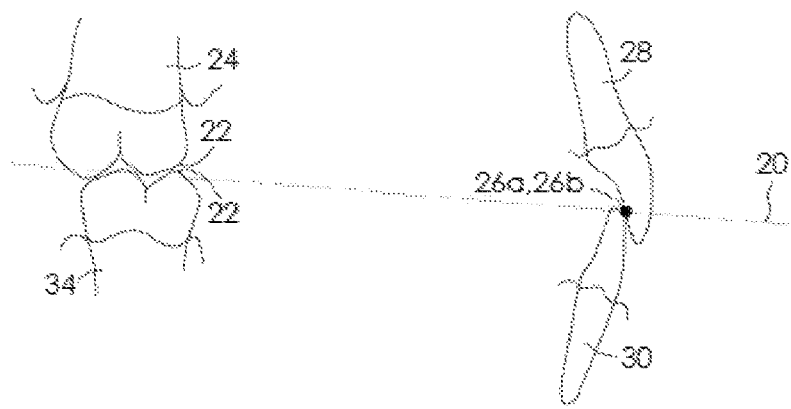
FIG. 3b is an elevation view of the natural occlusal plane represented by a portion of a global model of the jaw including a model of a patient's maxilla and mandible in a centric occlusion position and showing the incisor teeth and the premolar or molar teeth of the patient.
Figure 4:
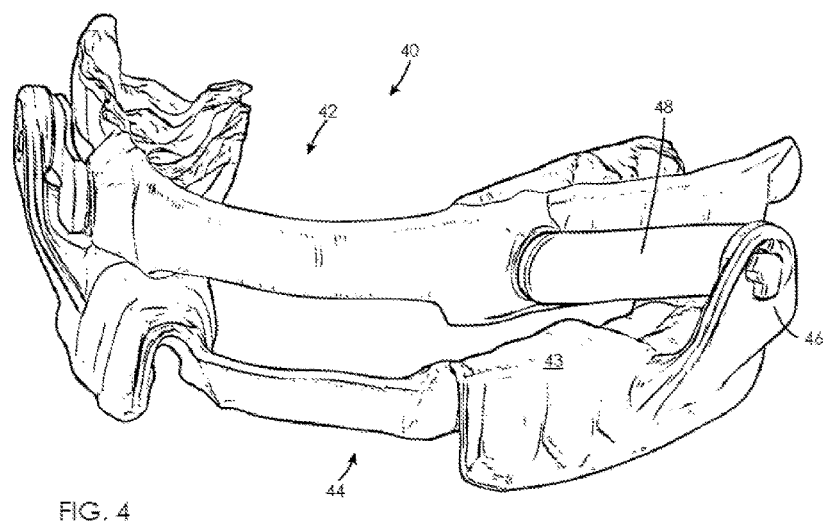
FIG. 4 is a perspective view of a mandibular advancement device according to one embodiment.

FIG. 4 shows that a mandibular advancement device 40 comprises an upper (or maxillary) gutter 42 having a cavity designed to receive a patient's maxilla and a lower (or mandibular) gutter 44 having a cavity designed to receive the patient's mandible. Each gutter 42, 44 includes an occlusion surface, 43 (in FIG. 3, only the occlusion surface of the lower gutter 44 is shown), i.e. the surfaces of the gutters that are in contact in the occlusion position. In the posterior sections, the lower gutter 44 comprises two extensions 46, extending towards the upper gutter 42 from the external surfaces. In the embodiment shown, these two extensions extend beyond the occlusion surface 43 of the lower gutter 44.

The upper 42 and lower 44 gutters are connected by two retaining pins (or rods) 48. The ends of the retaining pins 48 are connected in a hinged manner to the upper 42 and lower 44 gutters. More particularly, the retaining pins 48 engage the extensions 46 of the lower gutter 44. In one embodiment, the retaining pins 48 comprise heads (not shown) that engage in openings (not shown) defined respectively in the anterior section of the upper gutter 42 and in the extensions 46 of the lower gutter 44. In one embodiment, the heads of the retaining pins 48 and the openings are configured so that the retaining pins 48 cannot become detached from the gutters 42, 44 in normal positions of use. It will be appreciated that in alternative configurations (not shown), the means of attachment between the retaining pins 48 and the gutters 42, 44 can vary. As a non-limiting example, the retaining pins 48 can include female connectors while the gutters 42, 44 can include complementary male connectors.

In the embodiment shown in FIG. 4, the retaining pins 48 engage the extensions 46 from the interior to the exterior whereas they engage the upper gutter 42 from the exterior to the interior of the gutter 42.

As mentioned above, when a patient wears both gutters 42, 44 and the retaining pins 48 are connected thereto, the patient's mandible is configured in an advanced open position.

It will be appreciated that the device, illustrated in FIG. 4, is an example only of a mandibular advancement (or mandibular protrusion) device and many other variations thereof are possible.

Figure 5A:
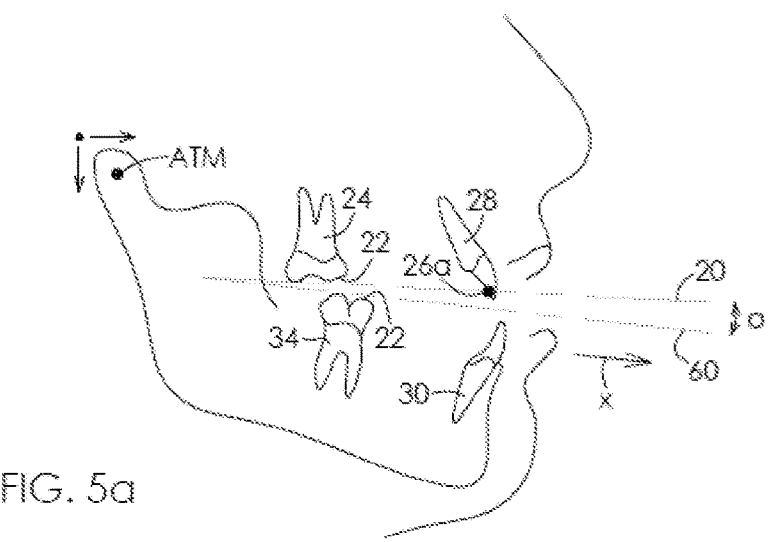
FIG. 5a is a schematic view of a patient's natural occlusal plane and an open-position occlusal plane of the mandible including the TMA.

As shown in FIG. 5, on opening the "O" articulation of a patient at the anterior teeth 28, 30, for example, by a height of one millimeter, the opening achieved at the posterior teeth 24, 34 is not one millimeter. In fact, the opening is not parallel to the dentition, which causes a change in the occlusal plane.

In dentistry, for certain patients, an anterior opening between the mandible and the maxilla of 1 mm can cause pain at the TMA. However, it is generally observed that, with time, the TMA becomes supple and the pain will disappear.

With a mandibular advancement device 40, the mandible is advanced forwards, along axis "X." When the mandible is advanced forwards, the anterior mandibular and maxillary teeth no longer fit together, which causes a marked disequilibrium of the TMA.

Moreover, to enable the advancement of the mandible, without creating interference between the mandibular and maxillary teeth, it is necessary, on average to open the articulation three to six millimeters. This "O" opening must be maintained every night.

With this "O" opening, the TMA is in an abnormal position, which can be uncomfortable for the patient. When keeping the mandible in an open and advanced position, the patient can move the mandible laterally, i.e. from left to right and vice versa. Moreover, for other patients, keeping the mandible in an open and advanced position causes bruxism and/or can induce the patient to open his mouth.

Figure 5B:
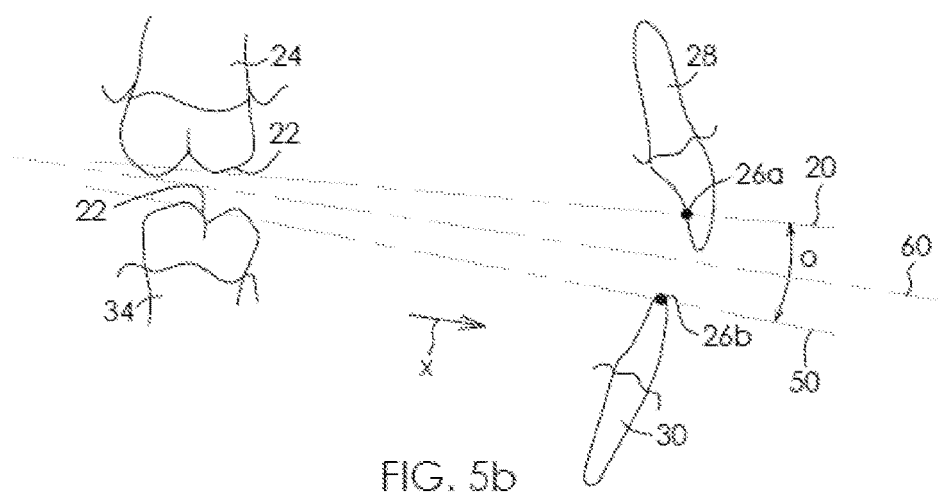
FIG. 5b is an elevation view of the patient's natural occlusal plane and the open-position occlusal plane of the mandible represented on the portion of the global model in FIG. 3b.

Keeping the mandible in an open position for a long period of time has the effect of creating a new occlusal plane 60, which differs from the natural occlusal plane 20, as shown in FIG. 5. This new occlusal plane is referred to as the "open-position occlusal plane" 60. It is calculated on the basis of the opening of the "O" occlusion. More particularly, the open-position occlusal plane 60 is calculated on the basis of the patient's natural occlusal plane 20 as well as the position of the mandible and maxilla in the open position. More particularly, the patient's natural occlusal plane 20 is represented by the line extending between the occlusal face 22 of the maxillary molars/premolars 24 and the contact point 26 on the maxillary incisors 28. The contact point on the maxillary incisors 28 corresponds to the contact point 26 between the maxillary 28 and mandibular 30 incisors in the occlusion position (FIG. 3). Based on the natural occlusal plane 20 shown when the mandible is in an open position, a virtual mandibular plane 50 is defined (FIG. 5*b*). This corresponds to a line extending between the occlusal face 22 of the mandibular molars/premolars 34 and the contact point on the mandibular incisors 30 (or tip of the mandibular incisors). The contact point on the mandibular incisors 30 corresponds to the contact point between the maxillary 28 and mandibular 30 incisors in the occlusion position (FIG. 3*b*). Based on the natural occlusal plane 20, shown in the open position and the virtual mandibular plane 50, the open-position occlusal plane 60 is determined. It corresponds to the center line between the natural occlusal plane 20 and the mandibular virtual plane 50, both anteriorly and posteriorly. Thus, in the open position, the angle defined between the natural occlusal plane 20 and the open-position occlusal plane 60 is substantially the same as the angle defined between the open-position occlusal plane 60 and the mandibular virtual plane 50. The greater the opening between the mandible and maxilla, the greater the difference between the patient's open-position occlusal plane 60 and natural occlusal plane 20.

Figure 6:
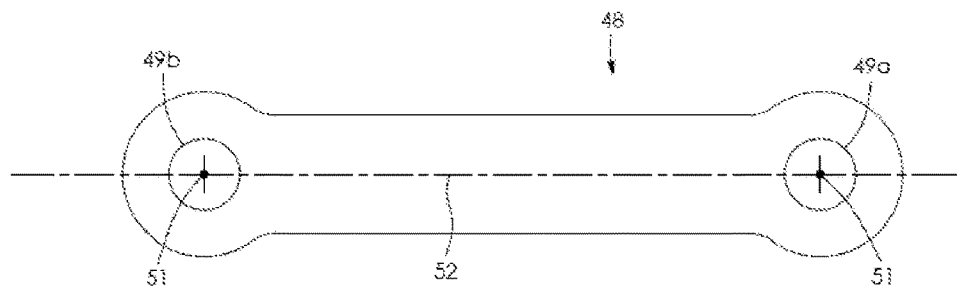
FIG. 6 is a front elevation view of a retaining pin of a mandibular advancement device according to one embodiment.

As mentioned above, the upper and lower (maxillary and mandibular) gutters 42, 44 are retained by retaining pins 48, which must work in the open-position occlusal plane 60 in order to protect the TMA. With reference to FIG. 6, a retaining pin 48 comprises two anchorage points 49*a*, 49*b*, spaced apart, to engage the upper and lower 42, 44 gutters respectively. More particularly, the upper gutter 42 is connected to the anterior anchorage point 49*a* of the retaining pin 48 whereas the lower gutter 44 is connected to the posterior anchorage point 49*b* of the retaining pin 48. Each of these anchorage points 49 is characterized by a center 51 with a centric line 52 extending between the two centers 51 of the anchorage points 49 of a retaining rod 48.

Figure 7:
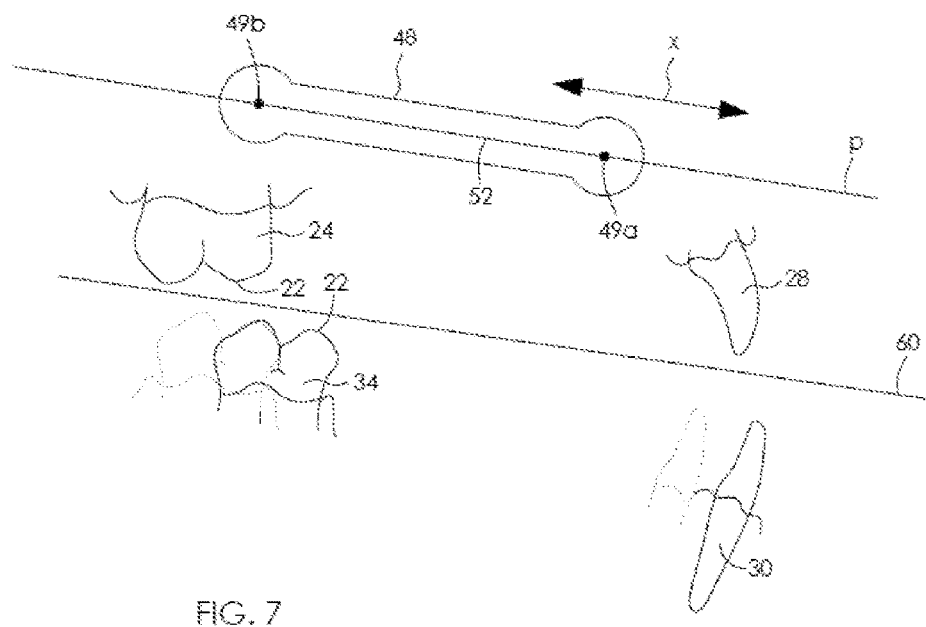
FIG. 7 is an elevation view of the retaining pin in FIG. 6 shown on the portion of the global model in FIG. 5b and extending parallel to the patient's open-position occlusal plane.

For the reasons described above, the advancement of the mandible affects the position of the condyle in the articular capsule. In order to minimize the side effects on the TMA, as shown in FIG. 7, in the proposed mandibular advancement device, the retaining rods 48 are held in a plane parallel and above the open-position occlusal plane 60, a plane created due to opening and keeping the mandible in the advanced position. More particularly, on aligning the retaining pins with the open-position occlusal plane 60, it has been observed that it is possible to reduce stress on the TMA. As will be described in further detail below, when wearing the mandibular protrusion device 40, the mandible in the advanced position slides, along axis X (FIG. 5*b*), parallel to the open-position occlusal plane 60, which differs from the natural occlusal plane 20, and on the occlusion surfaces of the upper and lower gutters 42, 44.

Figure 8:
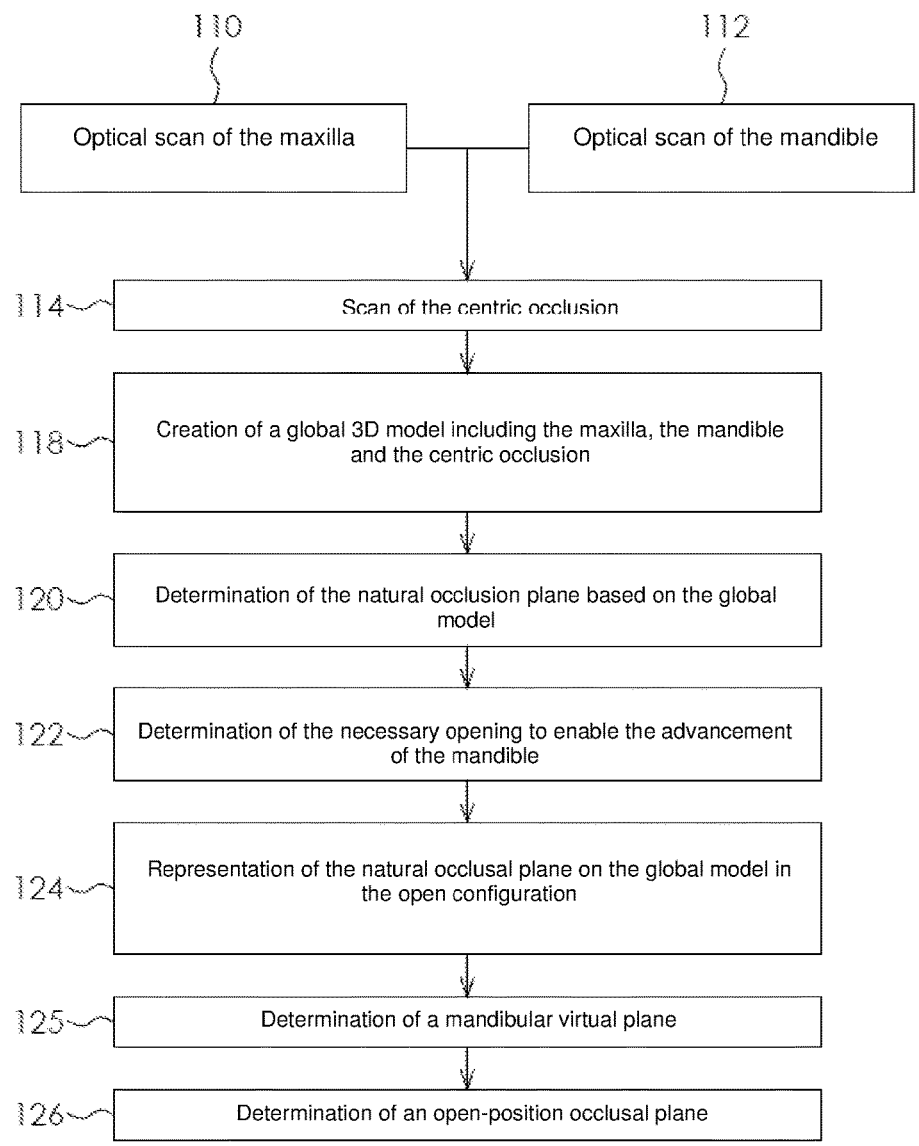
FIG. 8 is a schematic flowchart showing a method for determining a patient's open-position occlusal plane according to one embodiment.
Figure 9:
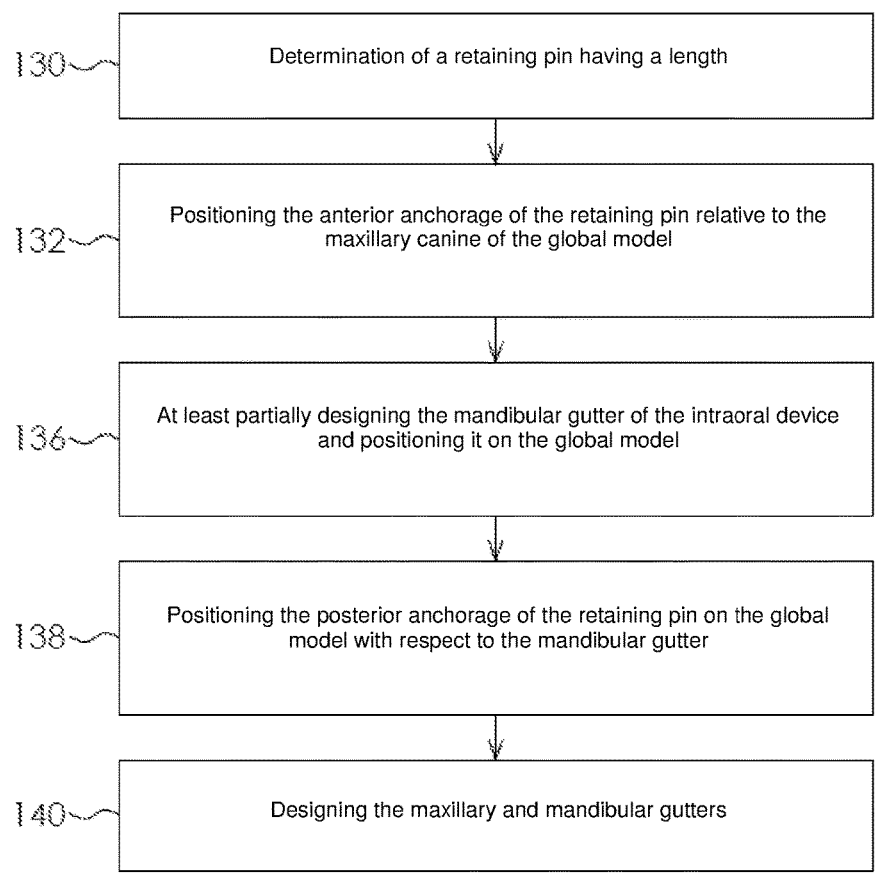
FIG. 9 is a schematic flowchart showing a method for designing a mandibular advancement device based on the open-position occlusal plane according to one embodiment.

With reference to FIGS. 8 and 9, a method of designing a mandibular advancement device 40 is described. This method can be implemented with the aid of a computer including specialized software and by means of a scanner. The specialized software can be designed to implement, at least partially, the method described below.

Firstly, with reference to FIGS. 7 and 8, the open-position occlusal plane 60 must be determined. In order to calculate the open-position occlusal plane 60, a digital model of the mouth must be obtained. This model can be obtained from an optical scan of the physical model, made of plaster for example, of the patient's mouth or from a scan made directly in the patient's mouth. By way of a non-limiting example, the scan can be made with the aid of intraoral optical cameras or a desktop scanner. The first step of scanning enables a three-dimensional (3D) computerized file to be created, including a model of the patient's dentition including the maxilla 110 and the mandible 112. These first models are stored in the computer's memory or any other support capable of containing these digital models.

Next, the "centric" occlusion, also referred to as "bite," must be modelled. Occlusion consists in the way in which the upper (maxillary) and lower (mandibular) teeth come into contact when the mouth is in the closed position. Centric occlusion consists in the manner in which the upper and lower teeth come into contact when the mouth is in a closed position and the mandible is in the centric position. Centric occlusion is the first contact of the teeth and may or may not coincide with the maximum intercuspation. This step 114 can be performed by scanning the two plaster models when they are configured in a centric position. This step 114 can also be performed directly in the patient's mount by asking him to close his mouth in centric occlusion and performing the scan with the aid of an intraoral optical camera, such as an optical scanner, while the mouth is in this position. This step 114 of scanning the centric occlusion allows a three-dimensional (3D) model of the patient's centric occlusion to be created, which will be used to articulate some models of the mandible and maxilla. This model is also stored in the memory of the computer or any other support that can contain digitalized models.

The models of the patient's maxilla, mandible and their centric occlusion are then combined, with the aid of the appropriate software, to create a global three-dimensional (3D) model of the jaw 118. This global model of the jaw is obtained in the form of a three-dimensional (3D) computerized file, including the combination of the models, which is stored in the memory of the computer or any other support capable of containing this global digitalized model. It represents the patient's dentition in a centric position in a virtual articulator. This articulator allows the computerized reproduction of the average movement of the mandible, i.e. the opening, closing, advancement and lateral movement (to the left and/or right). It will be used to determine the open-position occlusal plane 60.

Next, the patient's natural occlusal plane must be determined 120. The natural occlusal plane 20 is determined as the plane extending between the occlusal face of the maxillary molars/premolars 24 and the maxillary and mandibular contact points 26a, 26b on the maxillary incisors 28, as illustrated in FIG. 3. This plane can be determined with the aid of a computer including appropriate software and the global model of the jaw previously obtained combining, in the virtual articulator, the models of the maxilla and mandible. In order to determine the patient's natural occlusal plane 20, the mandible and maxilla are configured in a centric occlusion position in the global model of the jaw. The determination of the natural occlusal plane 20 includes identifying the contact points between the maxillary 24 and mandibular 34 molars/premolars and the contact points 26a, 26b between the maxillary 28 and mandibular 30 incisors.

Once the natural occlusal plane 20 in the centric occlusion position has been determined, the required "O" opening between the mandible and maxilla is determined 122. This "O" opening must be sufficient to allow the mandibular incisors 30 to be advanced without interfering with the maxillary incisors 28. This determination must be made by taking the necessary thickness of the material forming the upper and lower (42, 44) gutter into consideration. This can be estimated with the aid of the global model of the jaw as well as the computer including the specialized software. Based on this information, the models of the mandible and maxilla of the global model of the jaw are configured in an open position, corresponding to the "O" opening based on the information obtained in step 122.

With the global model of the jaw configured in an open position, a line, corresponding to the natural occlusal plane in an open position, is shown 124, as illustrated in FIG. 5. This line extends between the occlusal face 22 of the maxillary molars/premolars 24 and the maxillary contact point 26a on the maxillary incisors 28. Once more, this representation is made with the aid of the global model of the jaw and the specialized software included in the computer.

Next, a line extending between the occlusal face 32 of the mandibular molars/premolars 32 and the mandibular contact point 26b on the mandibular incisors 30 is determined 125. This step 125 consists in identifying the virtual mandibular plane 50 (FIG. 5).

The open-position occlusal plane 60 is determined with the aid of two lines (natural occlusal plane 20 represented in the open position (represented in step 124) and virtual mandibular plane 50 (step 125)) 126. It corresponds to the center line between the two lines 20, 50 as described above with reference to FIG. 5. It is therefore located midway between the natural occlusal plane 20 in the open position and the mandibular virtual plane 50. Once determined, the open-position occlusal plane 60 is represented on the global model of the jaw configured in an open position based on the "O" opening.

Now, with reference to FIG. 9, the mandibular advancement device 40 can be designed on the basis of the open-position occlusal plane 60. In order to design a mandibular advancement device 40 on the basis of the open-position occlusal plane 60, the mandible must be advanced according to the patient's maximum advancement. The patient's maximum advancement is determined and recorded by the dentist. For example, it is provided with the prescription for the mandibular advancement device. The maximum advancement is different for each patient. In order to achieve the advancement of the mandible according to the maximum advancement of the patient, the teeth of the mandible are slid along axis "X" (FIG. 5b) while respecting the open-position occlusal plane 60 previously determined.

Once the advancement has been achieved on the model, the retaining pins 48 that will be used with the device 40 will be selected. These are characterized by two anchorage points 49a, 49b each having a center 51, a centric line 52 extending between two centers 51 of the anchorage points 49a, 49b and a length determined by the length of the centric pin 52 between the two centers 51. If the centric line 52 is not provided during the identification of the retaining pins 48 to be used with the device 40, first of all it is determined with the aid of the specialized software. This centric line 52 of the retaining pins 48 will be used when positioning the retaining pins 48 in relation to the upper and lower gutters 42, 44. More particularly and, as described in further detail below, the centric line 52 of the retaining pins 48 will be positioned above the line of the open-position occlusal plane 60 and parallel thereto.

Although the method includes the positioning of two retaining pins 48, one for the right-hand side and one for the left-hand side of the device 40, the method described below relates to the positioning of one of the two retaining pins 48, the method being repeated for the other pin 48. The method described below allows the centric line 52 of the retaining pin 48 to be positioned above the line of the open-position occlusal plane 60 and parallel thereto.

Figure 10:
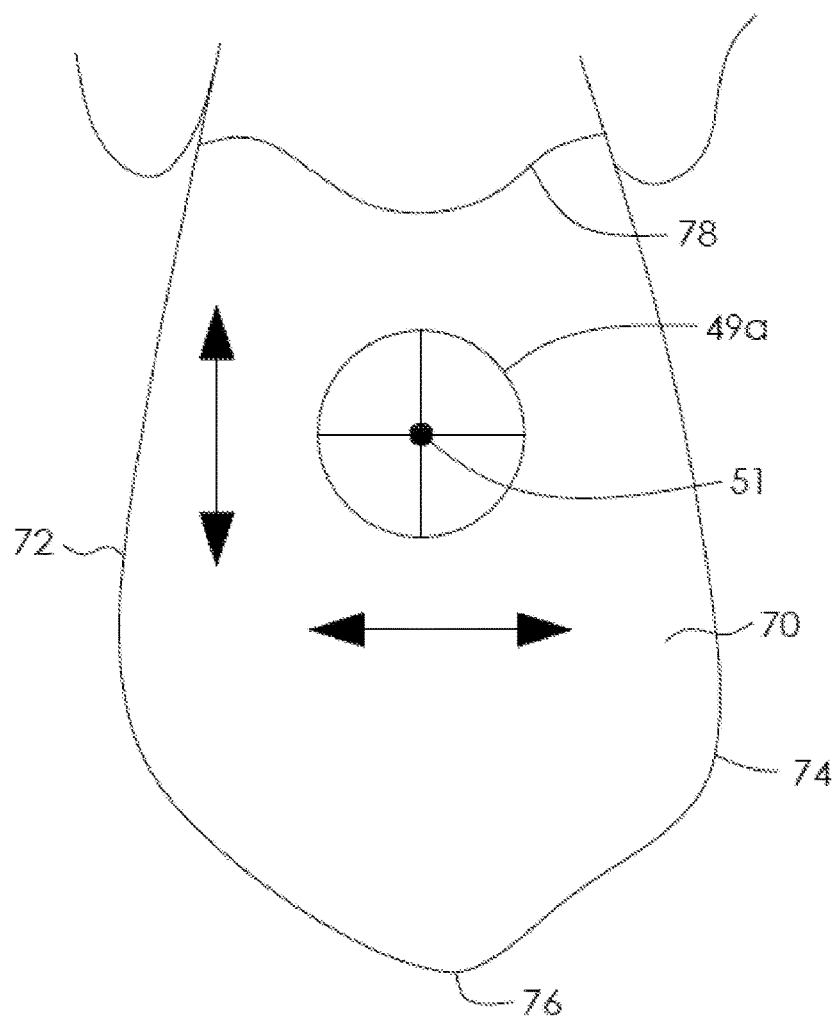
FIG. 10 is a front elevation view of a maxillary canine with a representation of an anterior anchorage point of the retaining pin.

The distance between the retaining pin 48 and the open-position occlusal plane 60 is at first determined, 130. This distance is typically between 4 and 15 mm and is shown by lines 80a, 80b in FIG. 11. In one embodiment, this distance is determined indirectly by positioning the center 51 of the anterior anchorage 49a of the retaining pin 48 relative to the maxillary canine 70 on the global model. In some embodiments, the center 51 of the anterior anchorage 49a is positioned 132 towards the middle third of the maxillary canine 70, as illustrated in FIG. 10. This positioning can be achieved with the aid of the specialized software under the control of the dental technician or another person skilled in the art.

A maxillary canine 70 features a distal side 72 (i.e. away from the middle, the side of a tooth that is closest to the posterior or back of the mouth), a mesial side (i.e. facing the middle, the side of a tooth that is closest to the anterior or front of the mouth), an incisor point 76, opposite a neck of the tooth 78. When positioning the center 51 of the anterior anchorage 49a of the retaining pin 48 relative to the patient's maxillary canine 70, 132, the technician can move the center 51 either towards the mesial side 74, or towards the distal side 72, or towards the incisor point 76, or towards the neck of the tooth 78.

The next step comprises designing the support, i.e. the extension 46, of the retaining pin 48 on the lower gutter 44. Once the position of the anterior anchorage 49a of the retaining pin 48 has been determined (step 132), the form of the extension 46, which will serve to anchor the retaining pin 48 to the lower gutter 44, is then constructed (step 136).

The length of the retaining pin 48 is determined on the basis of the patient's maximum advancement. This length varies depending on the patient. The retaining pin 48 is then positioned according to step 132 and parallel to the open-position occlusal plane 60.

As mentioned above, the posterior anchorage 49b of the retaining pin 48 is connected to the lower gutter 44 and, in one embodiment, to one of the extensions 46 of the lower gutter 44. Consequently, the lower gutter 44 of the device must be at least partially designed by including the section to which the posterior anchorage 49b of the retaining pin 48 will be connected.

The position of the posterior anchorage 49b of the retaining pin 48 and, consequently, the extension 46, if applicable, depends on the length of retaining pin 48 chosen, i.e. the length of the centric line 52. The length of the retaining pin 48 will serve as an advancement starting section from the anterior anchorage position. More particularly, with the aid of the global model in which the articulated maxilla and mandible are positioned in an open and advanced position, the retaining pin 48 is positioned 138 parallel to the open-position occlusal plane 60, extending towards the posterior section of the gutter 44 from the position of the anterior anchorage of the retaining pin 48. This positioning of the retaining pin can be achieved with the aid of the specialized software and the global model. This step 138 allows the anchorage point of the retaining rod on the lower gutter 44 and, in one embodiment, on the extensions 46 of the lower gutter 44, to be determined so that they extend parallel to the open-position occlusal plane 60.

Figure 11:
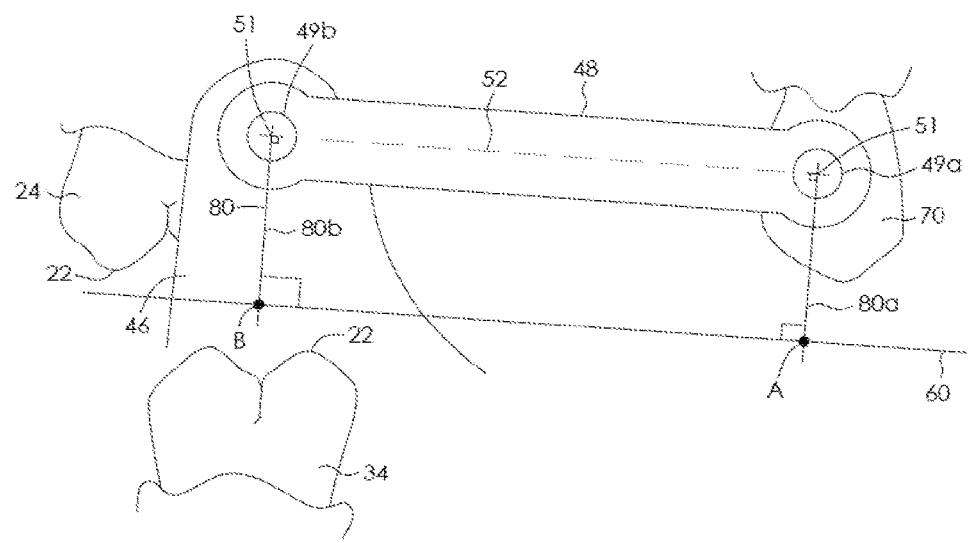
FIG. 11 is a side elevation view of a portion of the global model of the jaw including a representation of a posterior extension of the mandibular advancement device and a retaining pin with anterior and posterior anchorages positioned on the maxillary canine and on the posterior extension of the portion of the global model of the jaw respectively.

More particularly, in one embodiment, with reference to FIG. 11, with the aid of geometric calculations, the position of the posterior anchorage point 49b of the retaining pin 48 is determined 138 on the basis of: the anterior anchorage position 49a of the retaining pin 48, the length of the centric line 52 of the retaining pin 49 and the position of the open-position occlusal plane 60. As shown in FIG. 11, right angles (90°) are defined between two lines 80a, 80b extending perpendicular to the open-position occlusal plane 60, towards the maxilla, and the centric line 52 of the retaining pin 48.

More particularly, in one embodiment, the positioning of the anterior anchorage 49a of the upper gutter 42 and the posterior anchorage 49b of the lower gutter 44 is achieved in the following manner. As mentioned above, firstly the position of the anterior anchorage point 49a of the retaining pins 48 of the upper gutter 42 at the canines 70 is determined (step 136). This point 49a is generally located in the middle third or cervical third. When the anterior anchorage 49a is positioned on the global model in which the articulated maxilla and mandible are positioned in the open and advanced position, the software projects the line 80a from the center 51 of the anterior anchorage point 49a towards the line representing the open-position occlusal plane 60 so that the line 80a is perpendicular (defining an angle of 90°) to the open-position occlusal plane 60 (point A), the software determines a point (point B), by translation in the posterior direction and along the open-position occlusal plane 60. The distance of the translation in the posterior direction and along the open-position occlusal plane 60 from the intersection between the line 80a and the open-position occlusal plane 60 is determined by the length of the centric line 52 (between the two centers 51). From this new point B, the software determines the posterior anchorage point 49b (step 138) on the lower gutter 44, performing an upward translation, perpendicularly to the open-position occlusal plane 60, along the line 80b. The translation distance is determined by the length of the line 80a or the translation is performed up to the intersection with the centric line 52 of the retaining pin 48, which extends parallel to the open-position occlusal plane 60. Since the retaining pin 48 extends parallel to the open-position occlusal plane 60, the lines 80a and 80b are of the same length and extend perpendicularly to the centric line 52 of the retaining pin 48 and to the open-position occlusal plane 60.

Thus the retaining pin 48 will be above the open-position occlusal plane 60, above the natural occlusal plane 20 and will extend parallel to the open-position occlusal plane 60.

When the posterior anchorage position 49b is determined, the software, with the collaboration of a person skilled in the art such as a dental technician, completes the design of the upper 42 and lower 44 gutters (step 140). In this step, the geometric shape of the extension 46 connecting the posterior anchorage point 49b to the lower gutter 44 is determined.

Figure 12:
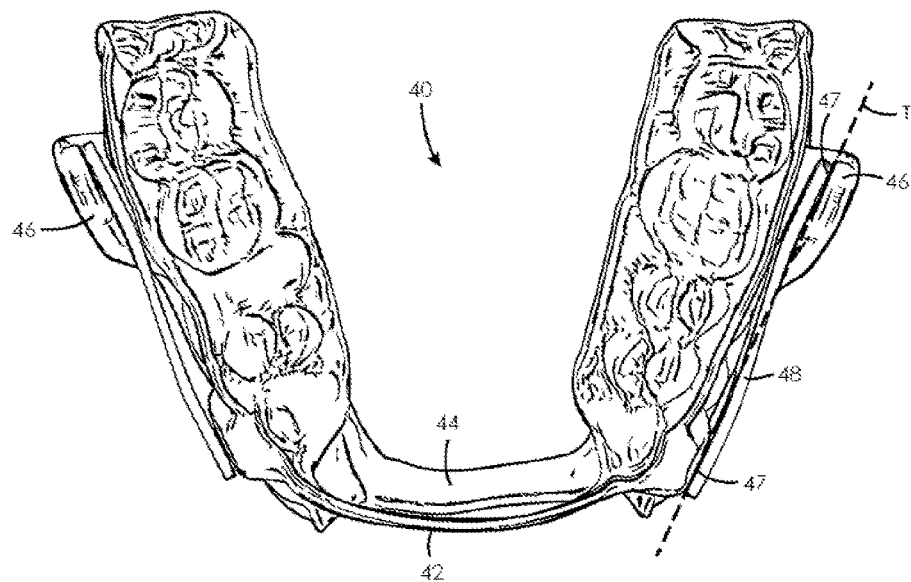
FIG. 12 is a top elevation view of the mandibular advancement device in FIG. 4, according to one embodiment.

Always with the aim of protecting the TMA, this invention also ensures that there is substantially no stress on the retaining pins due to anchorages being in opposing positions. With reference to FIG. 12, which is a top view of an device 40 designed according to the proposed method, the surfaces 47 of the anterior 49a and posterior 49b anchorages, in which the ends of the retaining pins 48 are engaged, extend substantially parallel to one another. In the embodiment shown, the two surfaces 47 are parallel and aligned along the axis "T." However, in an alternative embodiment (not shown), the two surfaces 47 can be parallel but not aligned along the same axis. Thus, it is possible to position the anterior 49a and posterior 49b anchorages by respecting the original shape of the retaining pins 48. When the mandible is in the advancement position, i.e. when the device 40 is being worn, it is important that the device 40 keeps the mandible in a centric position as easily as possible, i.e. by minimizing the stresses. If the device 40 tries to position itself outside the centric position and moves the mandible laterally, either to the left or right, the muscles of the TMA will then undergo increased stress. By designing the device so that the surfaces 47 of the anterior 49a and posterior 49b anchorages extend substantially parallel to one another, the stresses in the retaining rods 48 are reduced.

Once designed by the method described above, the mandibular advancement device 40 improves the preservation of the TMA, in an open and advanced position, along the open-position occlusal plane 60. More particularly, the retaining rods 48 are positioned substantially parallel and above the open-position occlusal plane 60. Thus, the design method, which can be implemented by using specialized 3D software, allows the open-position occlusal plane 60 to be determined mathematically and the retaining pins 48 to be positioned substantially parallel to and above the open-position occlusal plane 60. Thus the retaining pins 48 work in a plane parallel to the open-position occlusal plane 60.

Figure 13:
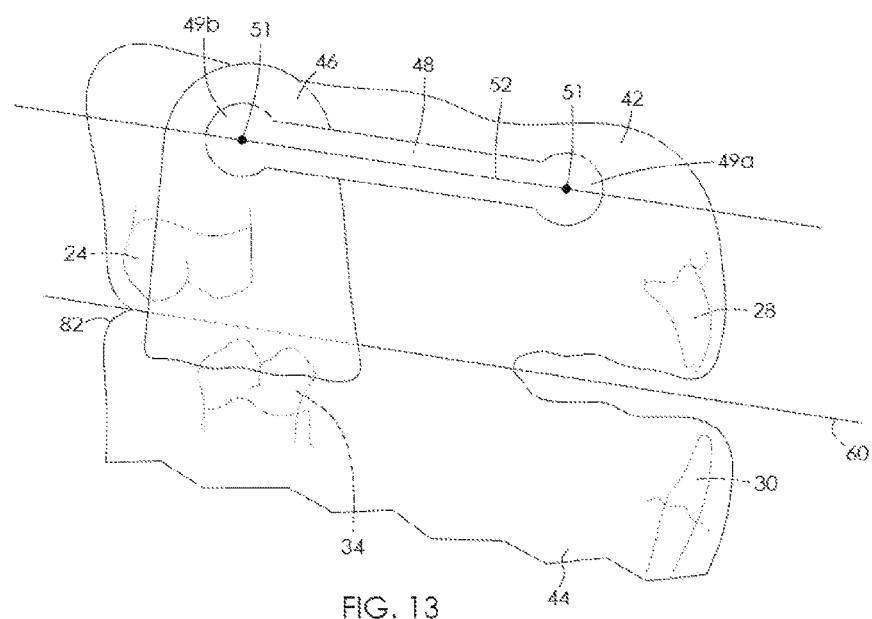
FIG. 13 is a schematic side elevation view of a portion of the mandibular advancement device designed by the method, according to one embodiment.

Referring to FIG. 13, in order to reduce the friction on the posterior teeth and promote working in a plane parallel to the open-position occlusal plane 60, during the step of designing the upper 42 and mandibular 44 gutters (step 140), these can be designed with flat surfaces at the occlusion faces of the posterior teeth. Thus the four occlusion faces of the upper 42 and lower 44 gutters at the posterior teeth are also in the same plane as the open-position occlusal plane 60.

More particularly, the upper gutter 42 includes, in the posterior sections, two flat surfaces 82 (only one flat surface is shown in FIG. 13), i.e. one flat surface located on the right-hand posterior side and one flat surface located on the left-hand posterior side. In one embodiment, these extend from the maxillary canine 70 and posteriorly to the distal of the first premolar or the distal of the second premolar. In one embodiment, the flat surfaces 82 extend posteriorly at most to the distal of the second premolar.

The other two flat surfaces 82 are located on the lower gutter 44 (only one flat surface is shown in FIG. 13), i.e. one flat surface located on the right-hand posterior side and one flat surface located on the left-hand posterior side. In one embodiment, they extend from the first premolar to the distal of the first molar.

The four flat surfaces, 82 are in the same plane as the open-position occlusal plane 60 defined by the method described above, i.e. the planes are aligned.

When designing the gutters 42, 44 of the device 40, four flat surfaces 82 (or plateaux) are therefore created at the occlusal faces of the gutters 42, 44. These flat surfaces 82, aligned with the open-position occlusal plane 60 allow: 1) the opening determined to be maintained; and 2) sliding lateral movements without obstruction by the dental cuspids.

In one embodiment, the flat surfaces on the upper gutter 42 are slightly shorter (i.e. of smaller length) than the flat surfaces on the mandibular gutter 44. This difference in length reduces the forces applied to the TMA when wearing the device 40. Moreover, when the patient makes a lateral movement (i.e. from left to right), the mandible will slide, guided and supported on the open-position occlusal plane 60, a plane that is determined by the "O" opening of the mandible.

Figure 14:
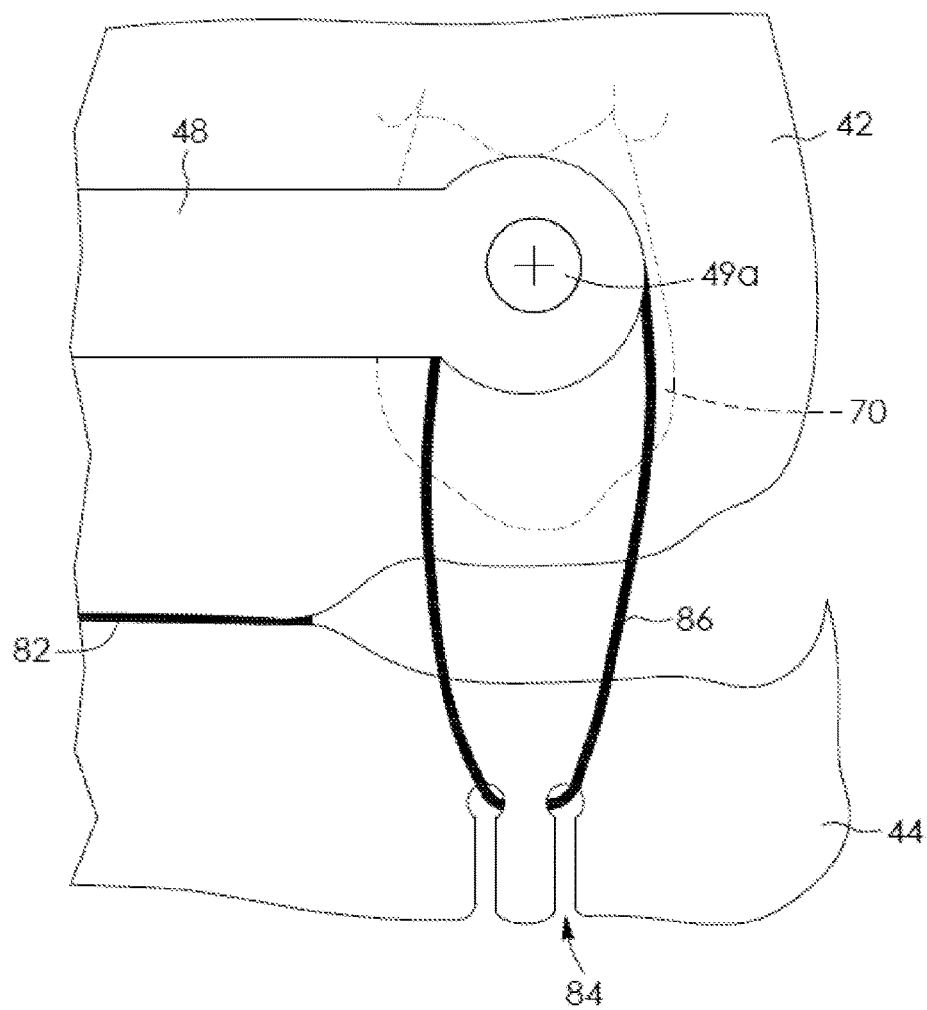
FIG. 14 is a schematic side elevation view of a portion of the mandibular advancement device designed by the method, including a system of attachment for the upper and lower gutters.

FIG. 14 shows that gutters 42, 44 can be built with other characteristics. For example, in the embodiment shown, the lower gutter 44 includes two slots 84 extending upwards from the lower edge of the lower gutter 44. A resilient member in the form of a loop 86, such as an elastic band, can be engaged in the two slots 84 and connected to the anterior anchorage 49a of the retaining pin 48 in order to control the opening of the gutters 42, 44 and prevent their detachment.

Thus, a method of designing a mandibular advancement device 40 is proposed and allows a mandibular advancement device 40 to be produced that protects the TMA by reducing the forces applied thereon. When wearing the mandibular advancement device 40 designed by the method described above, the retaining pins 48 work in the open-position occlusal plane 60, which corresponds to the plane in which the TMA is located in the open position.

The mandibular advancement device 40 or the intraoral orthosis (or device) can be conceived and manufactured by anyone the manufacturing methods known to those skilled in the art.

Moreover, although the embodiments of the mandibular advancement device designed, as well as its components, consist in certain geometric configurations, as explained and described above, only some of these components and geometries are essential and so the majority of them must not be interpreted as being restrictive. As is obvious to a person skilled in the art, other components and cooperation between them, as well as other geometric configurations, can be used for the mandibular advancement device, as briefly explained above and as it is possible to infer for a person skilled in the art. Moreover, it will be appreciated that the positions of the description, such as "above," "below," "left," "right," and other similar positions, must be interpreted in the context of the Figures, unless stated otherwise, and must not be regarded as limiting.

Several alternative embodiments and examples have been described and illustrated above. The embodiments of the invention described above are given solely by way of example. A person skilled in the art will appreciate the characteristics of the individual embodiments, as well as the possible combinations and variations of the components. A person skilled in the art will also appreciate that any embodiments can be made in any combination whatsoever with the other embodiments described above. It will be appreciated that the invention can be embodied in other specific forms without departing from the spirit or main characteristics thereof. The embodiments described must be regarded in all aspects as illustrative and non-limiting and the invention is not limited to the details given. Thus, although specific embodiments have been illustrated and described, numerous modifications are apparent without departing from the spirit of the invention. The scope of the invention is thus limited solely by the scope of the claims.

The invention claimed is:

1. Method of manufacturing a mandibular advancement device for a patient including a lower gutter and an upper gutter, the method comprising:
   obtaining a global model of the patient's jaw including a model of the mandible and maxilla in articulation by at least one of scanning intraorally the patient's jaw and scanning a physical model of the patient's jaw;
   configuring the global model of the patient's jaw in a centric occlusion position;
   determining a natural occlusal plane of the patient from the global model of the patient's jaw in the centric occlusion position;
   determining a necessary opening to enable the advancement of the patient's mandible;
   configuring the model of the mandible and the model of the maxilla to be in an open position corresponding to the determined necessary opening;
   determining a mandibular virtual plane from the global model of the patient's jaw in an open position based on the necessary opening determined;
   positioning the mandibular virtual plane and the natural occlusal plane within the global model of the jaw in the open position configuration;
   determining an orientation of an open-position occlusal plane from the mandibular virtual plane and the natural occlusal plane positioned within the global model of the jaw in the open position configuration;
   determining retaining pins for the mandibular advancement device, the retaining pins having a centric line, an anterior anchorage, a posterior anchorage and a length L between the anterior anchorage and the posterior anchorage;
   positioning the anterior and posterior anchorages so that the centric line of the retaining pins extends in a substantially parallel manner above the patient's open-position occlusal plane;
   designing the lower gutter and the upper gutter of the device using the global model of the patient's jaw and in a manner such that the anterior anchorages of the retaining pins are connectable to the upper gutter and in a manner such that the posterior anchorages of the retaining pins are connectable to the lower gutter; and
   manufacturing the mandibular advancement device including the lower gutter and the upper gutter including the anterior and posterior anchorages of the retaining pins based on the designed lower gutter and the upper gutter.

2. The method as claimed in claim 1, comprising obtaining a patient's maximum advancement and positioning the model of the mandible and maxilla in the open position in an advanced position of the mandible by a movement along the open-position occlusal plane for a distance corresponding to the patient's maximum advancement and wherein determining the retaining pins and positioning the anterior and posterior anchorages is achieved on the model of the mandible and maxilla in the open advanced position using the patient's maximum advancement.

3. The method as claimed in claim 1, wherein positioning the anterior and posterior anchorages comprises:
positioning the anterior anchorage of each of the retaining pins in relation to a respective canine of maxillary canines on the global model of the jaw; and
positioning the posterior anchorage of each of the retaining pins in a manner such that the centric line of the retaining pins extends substantially parallel to the open-position occlusal plane on the global model of the patient's jaw.

4. The method as claimed in claim 3, wherein positioning the posterior anchorage comprises determining a posterior position to the anterior anchorage, by a distance corresponding to the length L, in a direction parallel to the open-position occlusal plane on the global model of the patient's jaw in the open position.

5. The method as claimed in claim 1, wherein determination of the orientation of the open-position occlusal plane comprises determining a center line between the mandibular virtual plane and the natural occlusal plane in the open position configuration, the center line extending between a posterior section and an anterior section of the global model of the patient's jaw.

6. The method as claimed in claim 5, wherein determination of the necessary opening comprises estimating a distance enabling incisors of the mandible to be advanced without interfering with incisors of the maxilla and representing the global model of the patient's jaw in the open position based on the determined necessary opening.

7. The method as claimed in claim 1, wherein determination of the patient's natural occlusal plane from the global model of the patient's jaw comprises: configuring the global model of the patient's jaw in the centric occlusion position and defining a line extending between occlusal faces of the teeth of the mandible and maxilla in contact, tangential to incisal edges, at cusp points of pre-molars and molars of upper jaw and lower jaw, the method further comprises defining a point of maxillary contact corresponding to the intersection of the natural occlusal plane on incisors of the maxilla in the centric occlusion position and a mandibular contact point corresponding to an intersection of the natural occlusal plane on incisors of the mandible in the centric occlusion position and wherein determination of the mandibular virtual plane in the open position comprises defining a line extending between the occlusal face of at least one of molars and premolars of the mandible and the mandibular contact point on the mandibular incisors.

8. The method as claimed in claim 7, wherein obtaining the global model of the jaw comprises:
obtaining a model of the mandible and a model of the maxilla;
obtaining a model of centric occlusion; and
combining the model of the mandible, the model of the maxilla and the model of the centric occlusion in order create the global model of the patient's jaw in which the models of the mandible and maxilla are in articulation.

9. The method as claimed in claim 8, wherein obtaining the model of the mandible and the model of the maxilla comprises: performing an optical scan of the mandible and maxilla intraorally or of a physical model of the mandible and maxilla and obtaining the centric occlusion model comprises performing an optical scan of the mandible and maxilla in the centric occlusion position intraorally or of the physical model of the mandible and maxilla in the centric occlusion position.

10. Mandibular advancement device comprising: an upper gutter and a lower gutter designed to cover at least partially and respectively teeth and/or upper and lower jaws, and two retaining pins connecting the lower gutter and the upper gutter, the retaining pins extending parallel to and over the open-position occlusal plane, determined by the method claimed in claim 1, the retaining pins being of a length enabling the lower jaw to be kept in an advanced position in relation to the upper jaw when wearing the device.

11. The mandibular advancement device as claimed in claim 10, wherein the lower gutter and the upper gutter comprise flat surfaces at occlusion faces of posterior teeth and the flat surfaces of the upper gutter are shorter than the flat surfaces of the lower gutter.

12. The mandibular advancement device as claimed in claim 11, the flat surfaces of the upper gutter extend approximately from a maxillary canine and posteriorly until at least a distal of a first premolar and the flat surfaces of the upper gutter extend posteriorly at most to a distal of a second premolar.

13. Mandibular advancement device comprising: an upper gutter and a lower gutter designed to cover at least partially and respectively teeth and/or upper and lower jaw, and two retaining pins connecting the lower gutter and the upper gutter; the lower gutter, the upper gutter, and the retaining pins being conceived by the method claimed in claim 1, and wherein the lower gutter and the upper gutter comprise flat surfaces at occlusion faces of posterior teeth.

14. The mandibular advancement device as claimed in claim 13, wherein the flat surfaces of the upper gutter are shorter than the flat surfaces of the lower gutter, the flat surfaces of the upper gutter extending approximately from a maxillary canine and posteriorly until at least a distal of a first premolar and the flat surfaces of the upper gutter extending posteriorly at most to a distal of a second premolar.

15. Mandibular advancement device comprising: an upper gutter and a lower gutter designed to cover at least partially and respectively teeth and/or upper and lower jaw, and two retaining pins connecting the lower gutter and the upper gutter, the upper gutter, the lower gutter and the retaining pins being designed according to the method as claimed in claim 1.

16. Intraoral device comprising:
an upper gutter and a lower gutter designed to cover at least partially and respectively teeth and/or upper and lower jaws, and two retaining rods connecting the lower gutter and the upper gutter and of a length enabling the lower jaw to be kept in an open and advanced position in relation to the upper jaw, the two retaining rods extending between an anterior section of the upper gutter and a posterior section of the lower gutter, the two retaining rods being positioned parallel to an open-position occlusal plane determined by an opening necessary to advance and keep the lower jaw in the open and advanced position.

17. The intraoral device as claimed in claim 16, wherein the lower gutter and the upper gutter comprise flat surfaces at occlusion faces of posterior teeth.

18. The intraoral device as claimed in claim 17, wherein the flat surfaces of the upper gutter are shorter than the flat surfaces of the lower gutter.

19. The intraoral device as claimed in claim 17, wherein the flat surfaces of the upper gutter extend approximately from a maxillary canine and posteriorly until at least a distal of a first premolar.

20. The intraoral device as claimed in claim 17, wherein the flat surfaces of the upper gutter extend posteriorly at most to a distal of a second premolar.

* * * * *

UNITED STATES PATENT AND TRADEMARK OFFICE
CERTIFICATE OF CORRECTION

PATENT NO. : 10,285,784 B2
APPLICATION NO. : 15/204640
DATED : May 14, 2019
INVENTOR(S) : Jean Robichaud It is certified that error appears in the above-identified patent and that said Letters Patent is hereby corrected as shown below:

In the Claims

At Column 14, Lines 44-45, "determining retaining pins for the mandibular advancement device, the retaining pins having a centric line" should be -- selecting or designing retaining rods for the mandibular advancement device, the retaining rods having a centric line --.

At Column 14, Line 56, "retaining pins" should be -- retaining rods --.

At Column 14, Line 58, "retaining pins" should be -- retaining rods --.

At Column 14, Lines 61-62, "retaining pins" should be -- retaining rods --.

At Column 15, Lines 2-3, "determining the retaining pins" should be -- selecting or designing the retaining rods --.

At Column 15, Lines 9-10, "retaining pins" should be -- retaining rods --.

At Column 15, Lines 12-14, "retaining pins in a manner such that the centric line of the retaining pins extends" should be -- retaining rods in such a manner such that the centric line of the retaining rods extends" --.

At Column 16, Line 8, "retaining pins" should be -- retaining rods --.

At Column 16, Line 9, "retaining pins" should be -- retaining rods --.

At Column 16, Line 11, "retaining pins" should be -- retaining rods --.

At Column 16, Line 29, "retaining pins" should be -- retaining rods --.

Signed and Sealed this
Seventeenth Day of March, 2020

Andrei Iancu
*Director of the United States Patent and Trademark Office*

CERTIFICATE OF CORRECTION (continued)
U.S. Pat. No. 10,285,784 B2

At Column 16, Lines 30-31, "retaining pins" should be -- retaining rods --.

At Column 16, Line 45, "retaining pins" should be -- retaining rods --.

At Column 16, Lines 46-47, "retaining pins" should be -- retaining rods --.